United States Patent
Dorovsky

(10) Patent No.: US 10,585,056 B2
(45) Date of Patent: Mar. 10, 2020

(54) FINDING COMBINED HYDROCARBON FRACTION AND POROSITY BY MEANS OF DIELECTRIC SPECTROSCOPY

(71) Applicant: Baker Hughes Incorporated, Houston, TX (US)

(72) Inventor: Vitaly Nikolaevich Dorovsky, Novosibirsk (RU)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 1046 days.

(21) Appl. No.: 14/443,316

(22) PCT Filed: Oct. 8, 2014

(86) PCT No.: PCT/RU2014/000756
§ 371 (c)(1),
(2) Date: May 15, 2015

(87) PCT Pub. No.: WO2016/056936
PCT Pub. Date: Apr. 14, 2016

(65) Prior Publication Data
US 2016/0299092 A1   Oct. 13, 2016

(51) Int. Cl.
*G01V 1/40* (2006.01)
*G01N 27/02* (2006.01)
(Continued)

(52) U.S. Cl.
CPC ............ *G01N 27/026* (2013.01); *G01V 3/28* (2013.01); *G01V 3/30* (2013.01); *G01V 3/38* (2013.01); *Y02A 90/344* (2018.01)

(58) Field of Classification Search
CPC ... G01V 3/30; G01V 3/38; G01V 3/28; G01V 3/08; G01V 3/18; G01N 27/026; E21B 41/0092; E21B 47/00; E21B 49/00
See application file for complete search history.

(56) References Cited

U.S. PATENT DOCUMENTS

2014/0019049 A1   1/2014   Dorovsky
2014/0025357 A1*  1/2014   Petersen .................. G01V 3/28
                                                      703/2
(Continued)

FOREIGN PATENT DOCUMENTS

WO   2012144979 A1   10/2012
WO   2013012349 A1   1/2013
WO   2015005818 A1   1/2015

OTHER PUBLICATIONS

Int'l Search Report and Written Opinion in PCT/RU2014/000756, dated Jun. 8, 2015.

*Primary Examiner* — Elias Desta
(74) *Attorney, Agent, or Firm* — Mossman, Kumar & Tyler PC

(57) ABSTRACT

Methods, systems, devices and products for evaluating an earth formation comprising a porous medium. Methods include estimating at least one property of the earth formation using a plurality of estimates of complex permittivity based on measurements using an electromagnetic tool at a plurality of frequencies in a borehole penetrating the earth formation while the porous medium is saturated with a mixture of water and a plurality of hydrocarbon phases including oil and gas by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate.

16 Claims, 10 Drawing Sheets

(51) Int. Cl.
*G01V 3/30* (2006.01)
*G01V 3/38* (2006.01)
*G01V 3/28* (2006.01)

(56) References Cited

U.S. PATENT DOCUMENTS

| | | | |
|---|---|---|---|
| 2015/0127264 A1* | 5/2015 | Hadj-Sassi | G01V 3/30 702/7 |
| 2016/0097876 A1* | 4/2016 | Freed | G01V 3/24 703/2 |
| 2017/0082776 A1* | 3/2017 | Frey | G01V 3/30 |
| 2017/0351000 A1* | 12/2017 | Marsala | G01V 3/20 |

* cited by examiner

FINDING COMBINED HYDROCARBON FRACTION AND POROSITY BY MEANS OF DIELECTRIC SPECTROSCOPY

BACKGROUND OF THE DISCLOSURE

1. Field of the Disclosure

This disclosure generally relates to exploration and production of hydrocarbons involving investigations of regions of an earth formation penetrated by a borehole. More specifically, the disclosure relates to the dielectric spectroscopy of an earth formation using a logging tool in a borehole.

2. Description of the Related Art

Electrical earth borehole logging is well known to persons having an ordinary level of skill in the art, and various devices and various techniques have been described for this purpose. Broadly speaking, there are two categories of electrical logging apparatus. In the first category, one or more measurement electrodes current source(s) or sink(s) are used in conjunction with a return electrode (which may be a diffuse electrode such as a logging tool's body or mandrel). A measurement current flows in a circuit that connects a current source to the measurement electrode(s), through the earth formation to the return electrode, and back to the current source in the tool. In a second category, that of inductive measuring tools, an antenna within the measuring instrument induces a current flow within the earth formation. The magnitude of the induced current is detected using either the same antenna or a separate receiver antenna. The present disclosure belongs to the second category.

SUMMARY OF THE DISCLOSURE

In view of the foregoing, the present disclosure is directed to a method and apparatus for estimating at least one property of an earth formation including a porous medium using dielectric spectroscopy of subterranean formations penetrated by a borehole in the earth formation.

One embodiment according to the present disclosure includes a method of evaluating an earth formation including a porous medium. The method may include making a plurality of estimates of complex permittivity ($\varepsilon$) based on measurements using an electromagnetic tool at a plurality of frequencies in a borehole penetrating the earth formation while the porous medium of the formation is saturated with a mixture of water and a plurality of hydrocarbon phases including oil and gas; and estimating a parameter of interest of the earth formation using the plurality of estimates by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate.

The method may further include generating a spectral dielectric curve by mapping the real part with respect to the imaginary part for each estimate of the plurality of estimates. The spectral dielectric curve constant (v) may be calculated using a maximum imaginary value for the spectral dielectric curve and asymptotic values ($\varepsilon=\varepsilon_0$, $\varepsilon=\varepsilon_\infty$) for the real parts of each estimate of the spectral dielectric curve. The method may include using a model correlating the plurality of estimates to a Havriliak-Negami relaxation curve to determine a value for at least one polarization parameter associated with the curve. The at least one polarization parameter may comprise $\beta$, wherein $\beta$ relates to a degree of saturation of the porous medium with the plurality of hydrocarbon phases in the presence of water. The method may include determining the value for $\beta$ using an angle of intersection ($\varphi$) of two curves Im $\varepsilon=\Phi(\text{Re }\varepsilon)$ and Im $\varepsilon=0$ at the point where $\varepsilon=\varepsilon_0$ and a second angle of intersection ($\psi$) of the two curves Im $\varepsilon=\Phi(\text{Re }\varepsilon)$ and Im $\varepsilon=0$ at the point where $\varepsilon=\varepsilon_\infty$. The method may include using the spectral dielectric curve constant (v) and the value for $\beta$ to determine a value for another polarization parameter $\alpha$, wherein $\alpha$ relates to a degree of saturation of the porous medium with water, and wherein $\alpha$ relates to a polarization angle. The method may include determining values $\alpha_0$ and $\alpha_*$ for $\alpha$ using a relationship defining $\alpha$ as a function of $\beta$, wherein $\alpha_0$ corresponds to the value for $\beta$ ($\beta_0$) and $\alpha_*$ corresponds to a second value for beta correlated with a state of the porous medium free from the plurality of hydrocarbon phases.

The at least one property may include at least one of: i) combined hydrocarbon fraction, ii) water fraction, and iii) porosity. The method may include using the values $\alpha_0$ and $\alpha_*$ to estimate a bulk water fraction of the porous medium or a bulk hydrocarbon fraction of the porous medium. The method may include determining a value $\alpha_*$ for a using a relationship defining $\alpha$ as a function of $\beta$, wherein $\alpha_*$ corresponds to a second value for beta correlated with a state of the porous medium free from the plurality of hydrocarbon phases; and using the value $\alpha_*$ to estimate a porosity of the porous medium.

The method may also include conveying the electromagnetic tool in the borehole. The electromagnetic tool may use electrical induction. The method may also include using the electromagnetic tool for making the measurements at the plurality of frequencies.

One embodiment according to the present disclosure includes an apparatus for evaluating an earth formation. The apparatus may include a carrier configured to be conveyed in a borehole penetrating the earth formation; an electromagnetic tool disposed on the carrier and configured to make measurements indicative of an imaginary part and a real part of a permittivity of the earth formation at a plurality of frequencies; and at least one processor. The at least one processor may be configured to perform methods as described above, including: making a plurality of estimates of complex permittivity ($\varepsilon$) based on measurements using an electromagnetic tool at a plurality of frequencies in a borehole penetrating the earth formation while the porous medium of the formation is saturated with a mixture of water and a plurality of hydrocarbon phases including oil and gas; and estimating a parameter of interest of the earth formation using the plurality of estimates by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate. One embodiment includes a non-transitory computer-readable medium product having instructions thereon that, when executed, causes the at least one processor to perform the method. Further embodiments include a non-transitory computer-readable medium product having instructions thereon that, when executed, causes the at least one processor to perform a method comprising estimating a parameter of interest of the earth formation using the plurality of estimates by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate. The non-transitory computer-readable medium product may include at least one of: (i) a ROM, (ii) an EPROM, (iii) an EEPROM, (iv) a flash memory, or (v) an optical disk.

BRIEF DESCRIPTION OF THE DRAWINGS

The present disclosure is best understood with reference to the accompanying figures in which like numerals refer to like elements and in which.

DETAILED DESCRIPTION OF THE DISCLOSURE

Figure 1:
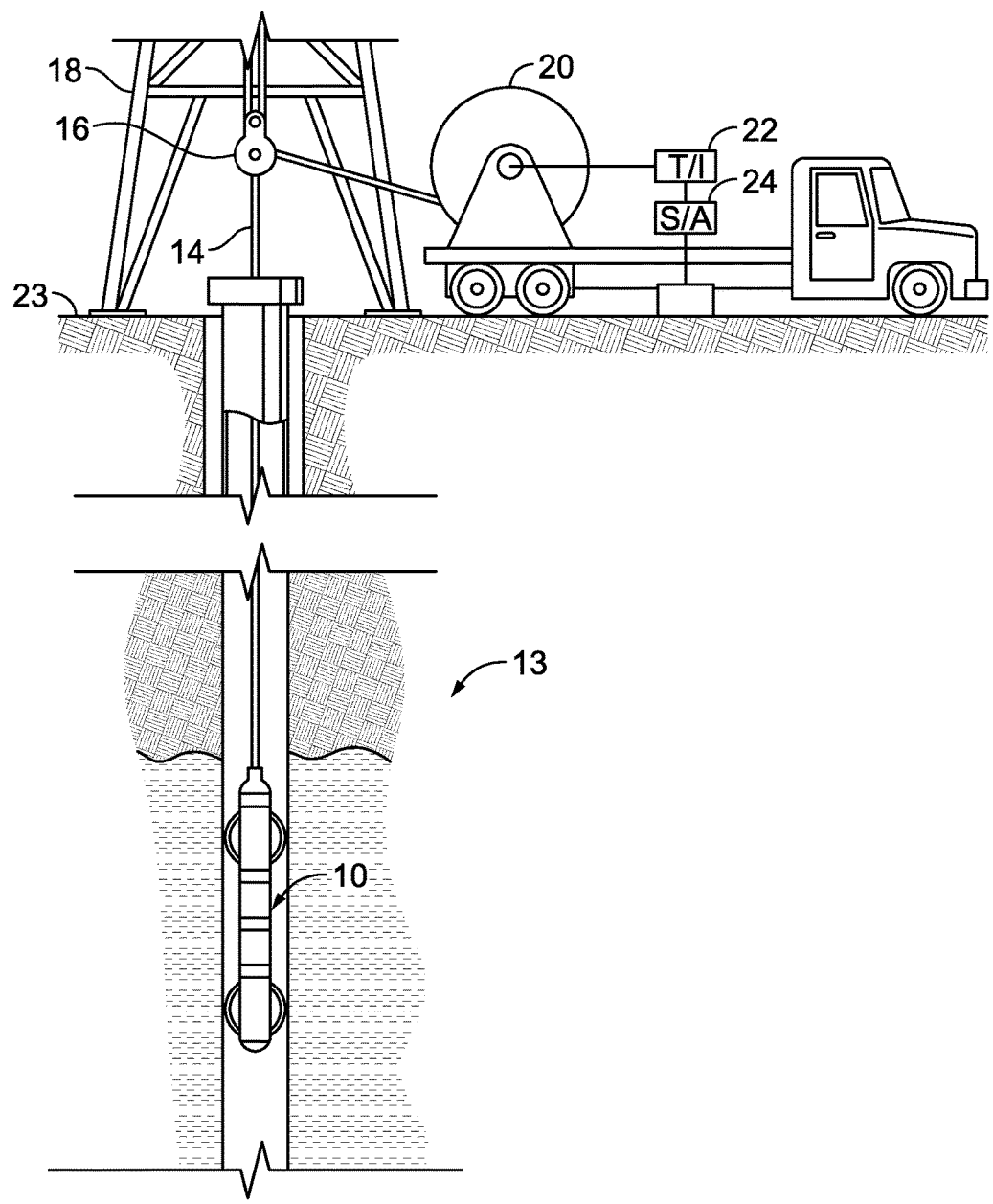
FIG. 1 is a schematic of a drilling site including an electromagnetic tool for estimating a parameter in an earth formation according to one embodiment of the present disclosure.

In the disclosure that follows, in the interest of clarity, not all features of actual implementations are described. It will of course be appreciated that in the development of any such actual implementation, as in any such project, numerous engineering and technical decisions must be made to achieve the developers' specific goals and subgoals (e.g., compliance with system and technical constraints), which will vary from one implementation to another. Moreover, attention will necessarily be paid to proper engineering and programming practices for the environment in question. It will be appreciated that such development efforts may be complex and time-consuming, outside the knowledge base of typical laymen, but would nevertheless be a routine undertaking for those of ordinary skill in the relevant fields.

Electrical earth borehole logging is well known in the art, and various devices and various techniques have been described for this purpose. Induction logging tools may operate by inducing a current flow within an earth formation and detecting the magnitude of the induced current, which is responsive to properties of the earth formation. Thus, it is well known that properties of an earth formation may be estimated using information acquired in induction logging.

In aspects of the disclosure, dielectric spectroscopy, and specifically the estimation of electric permittivity of a saturated medium of an earth formation, may be used to determine properties of the formation. An estimate of electric permittivity may include an imaginary part and a real part. It is known that each of the imaginary part and the real part of an estimate may vary in dependence upon the frequency of the electrical signal used in making the estimate. By making several estimates over a range of frequencies and characterizing the relationship of changes in both the real and imaginary parts of the estimates with frequency, information may be obtained about the state of the earth formation (e.g., porosity).

In aspects of the present disclosure, a parameter of interest of the earth formation may be estimated for earth formations including a porous medium saturated with a mixture of water and a plurality of hydrocarbon phases (e.g., oil and natural gas). Previous techniques for estimating parameters of interest such as fraction (or percentage) of water, porosity, and the like fail to produce acceptable results when the porous medium is saturated with this mixture.

The parameter of interest may be estimated using a plurality of estimates of complex permittivity at a plurality of frequencies. The parameter of interest may be estimated by using a spectral dielectric curve constant (v) for the porous medium. The spectral dielectric curve constant (v) is invariant with respect to a ratio of water to hydrocarbons in the porous medium and determined by an estimated rate of change between estimates of the plurality of estimates of complex permittivity of an imaginary part relative to a real part of each estimate.

In some aspects, electric permittivity may be estimated using an electromagnetic tool configured to generate an electric current at a plurality of frequencies. In embodiments, the electromagnetic tool may include an inductive electromagnetic probe that may be electrically coupled to an earth formation from inside of a borehole penetrating the earth formation. Dielectric permittivity may be obtained by solving Maxwell's equations. For a homogeneous medium, the relationship between a magnetic field, $H_z$, and dielectric permittivity, $\varepsilon$, may be expressed as:

$$H_r^0 = \frac{M_z rz}{4\pi R^5}(3 + 3kR + k^2 R^2)e^{-kR}, \quad (1)$$

$$H_\varphi^0 = 0,$$

$$H_z^0 = -\frac{M}{4\pi R^3}\left(\frac{3r^2}{R^2} + \frac{3kr^2}{R} + k^2 R^2 - 2 - 2kR\right)e^{-kR},$$

$$R^2 = r^2 + z^2,$$

$$k^2 = -\omega^2 \mu \varepsilon,$$

$$\varepsilon = \varepsilon' + i\varepsilon''.$$

where $M_z$ is the receiver coil magnetic moment, k is a wave number, $\omega$ is a circular ( ) frequency, R is a radial distance, r and z are coordinates in the cylindrical coordinate system, μ is the permeability of the material, and ε' and ε" are real and imaginary parts of dielectric permittivity. The dielectric permittivity may be estimated using methods known to those of skill in the art, including, but not limited to one or more of: (i) a Newton method and (ii) a Marquardt-Levenberg method.

The estimated imaginary and real parts of permittivity of the earth formation may then be used to estimate at least one parameter of interest of the earth formation. The at least one parameter of interest may include, but is not limited to: (i) percentage of mixed hydrocarbons; (ii) percentage of water; and (iii) formation porosity.

If, for example, a dipole antenna configured to emit electromagnetic waves is placed in the center of the borehole with a receiver antenna located in the borehole at a certain distance from the transmitter, then real and imaginary parts of the magnetic field may be measured by the receiver antenna. A spectral image of dielectric permittivity may be generated using the imaginary and real parts of permittivity over a plurality of frequencies. The spectral image may also be referred to as a "spectral dielectric curve" and a "polarization curve". Each point on the spectral image of dielectric permittivity may correspond to a specific frequency in the electromagnetic spectrum.

Aspects of the disclosure may include generating a spectral dielectric curve by mapping the real part with respect to the imaginary part for each estimate of the plurality of estimates. The bulk fractions of water and the hydrocarbon mixture in the earth formation may then be estimated using the spectral dielectric curve (spectral image) of dielectric permittivity.

Aspects of the present disclosure include using a borehole inductive electromagnetic tool to measure the real and imaginary parts of the dielectric spectrum at a fixed borehole depth. This may include estimating all spectral characteristics of the Havriliak-Negami curve. The percentage of plurality of hydrocarbon phases contained in the formation pores may be estimated from hydrocarbon and/or water saturation characteristics using methods disclosed herein. Using the tabulated curves for sandstones, carbonates, etc. and the limit value of another polarization parameter, further aspects of the disclosure may enable estimation of the formation porosity. Example apparatus and method embodiments for estimating properties of the formation are discussed below.

FIG. 1 shows an electromagnetic tool 10 suspended, in a borehole 12 penetrating earth formation 13, from a suitable cable 14 that passes over a sheave 16 mounted on drilling rig 18. By industry standard, the cable 14 includes a stress member and seven conductors for transmitting commands to the tool and for receiving data back from the tool as well as power for the tool. The electromagnetic tool 10 is raised and lowered by draw works 20. Electronic module 22, on the surface 23, transmits the required operating commands downhole and in return, receives data back which may be recorded on an archival storage medium of any desired type for concurrent or later processing. The data may be transmitted in analog or digital form. Data processors such as a suitable computer 24, may be provided for performing data analysis in the field in real time or the recorded data may be sent to a processing center or both for post processing of the data. Some or all of the processing may also be done by using a downhole processor at a suitable location on the logging tool 10. While a wireline conveyance system has been shown, it should be understood that embodiments of the present disclosure may be utilized in connection with tools conveyed via rigid carriers (e.g., jointed tubular or coiled tubing) as well as non-rigid carriers (e.g., wireline, slickline, e-line, etc.). Some embodiments of the present disclosure may be deployed along with LWD/MWD tools.

The electromagnetic tool 10 may include at least one transmitting antenna and at least two receiving loop antennas mounted on a pad. The tool may be operated in at least two modes. A first mode may be referred to as Mini-MPR (Multiple propagation resistivity) mode that may measure attenuation and a phase difference between the two receivers. The electromagnetic tool 10 may also be operated in a second mode (an induction mode) in which a compensated magnetic field (voltage) may be measured. The current in the transmitter coil may induce a magnetic field in the earth formation 13. This magnetic field, in turn, may cause eddy currents to flow in the earth formation 13. Because of the presence of these formation currents, a magnetic field may be coupled into a receiver coil R thereby generating a receiver signal. Logging tools having "a receiver coil" and "a transmitter coil" each comprised of several coils arranged in a predetermined fashion to obtain a desired response may be used. The receiver signal may then be amplified and applied to one or more phase sensitive detectors (PSDs). Each PSD may detect a phase component signal having a phase identical to a phase reference signal which may also be applied to the detector. The phase reference signal may have a predetermined phase relationship to the current in the transmitter coil(s). The output of the PSD(s) may be further processed downhole, or may be sent uphole to surface equipment for processing or display to an operating engineer.

In the induction mode, one receiver loop coil may serve as a main receiver and the other as a bucking receiver. The transmitting antennas may include loops and/or electric dipoles. For loop transmitter antennas, the transmitters and receivers may be in one of three orientations. If the z-axis of the tool is parallel to the longitudinal axis of the tool, then the x-axis may be radial through the center of the pad, and the y-axis may be tangential to the pad. The zz-component may refer to a z-source and a z-receiver and so on. In some embodiments, xx-transmitters and receivers may be used.

Figure 2A:
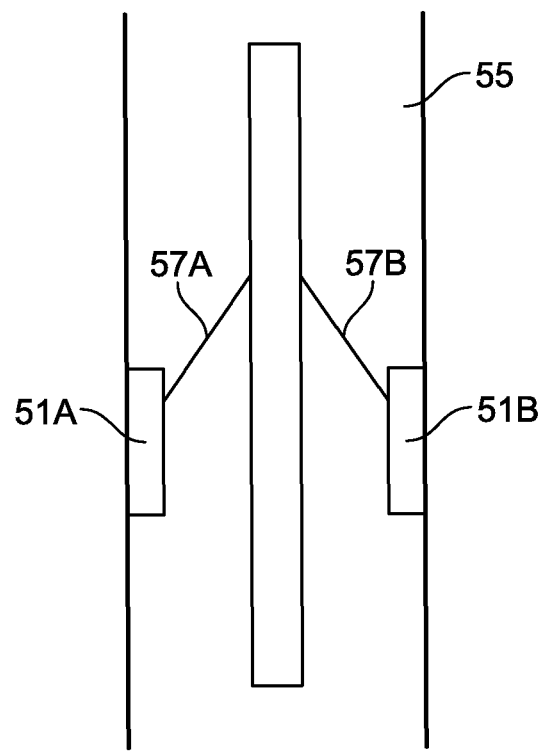
FIG. 2A is a schematic view of an electromagnetic tool in accordance with one embodiment of the present disclosure.

FIG. 2A shows an electromagnetic tool 10 for one embodiment according to the present disclosure. The electromagnetic tool 10 may include a body 55 with two pads 51A, 51B extended on extension devices 53A, 53B. Two pads are shown for illustrative purposes and, in actual practice, there may be more pads. The extension devices 53A, 53B may be electrically operated, electromechanically operated, mechanically operated or hydraulically operated. With the extension devices 53A, 53B fully extended, the pads 51A, 51B can make contact with the borehole wall (not shown) and make measurements indicative of properties of the borehole wall. Orientation sensors (not shown) may provide an indication of the orientation of the electromagnetic tool 10. In addition, cable depth measurements may be obtained using a sensor (not shown) at the surface that measures the amount of cable spooled out. In addition, accelerometers may be used downhole to provide other measurements indicative of the depth of the electromagnetic tool 10. The orientation sensors may include accelerometers, magnetometers or gyroscopes. Depth may also be estimated from a gyro output.

Figure 2B:
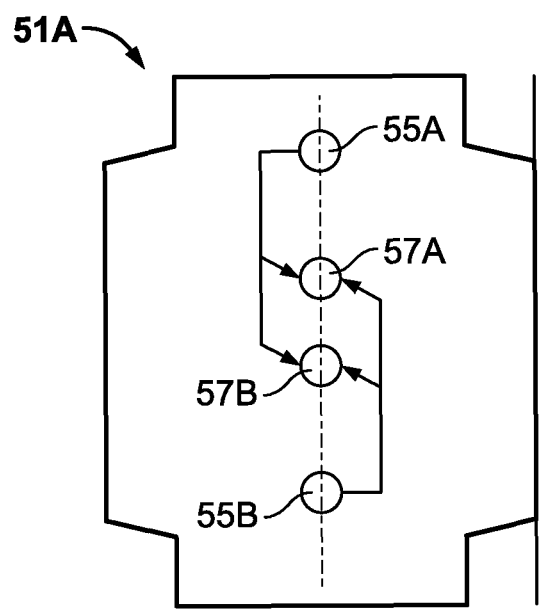
FIG. 2B is a schematic view of a pad of an electromagnetic tool in accordance with one embodiment of the present disclosure.

An exemplary arrangement of dual transmitters and receivers on each of the pads is shown in FIG. 2B. Shown therein is pad 51A with two transmitters 55A, 55B disposed about two receivers 57A, 57B. Also depicted schematically by arrows in FIG. 2B are measurements that may be made by each of the two receivers 57A, 57B corresponding to signals generated by each of the two transmitters 55A, 55B.

The use of dual transmitters may provide a symmetrical response. The use of dual transmitters may also reduce effects of borehole rugosity. Also, the use of dual transmitters may reduce electronics-related errors in attenuation measurement. The electronics-related errors may not affect the phase difference measurement.

When in the Mini-MPR mode, the two transmitters 55A, 55B may be placed symmetrically with respect to the receiver antennas 57A, 57B. Attenuation and phase difference are measured for each of the transmitters 55A, 55B. The measurements may be averaged to give the final readings:

$$Att = \frac{Att_{T1} + Att_{T2}}{2}; \quad (2)$$

$$Pha = \frac{Pha_{T1} + Pha_{T2}}{2}$$

where the subscripts T1 and T2 denote the first and second receivers. Assuming a uniform earth formation for which the magnetic fields at the receiver locations are $H_1$ and $H_2$ and assuming that the two receivers have gains $G_1$ and $G_2$, the ratio of the two receiver outputs $R_{T1}$ for the 1st transmitter may be derived from the ratio:

$$R_{T1} = \frac{G_2 H_2}{G_1 H_1} = \frac{G_2}{G_1} \frac{A_2}{A_1} e^{i\Delta\phi} \quad (3)$$

where $A_1$ and $A_2$ are the amplitudes of $H_1$ and $H_2$, respectively; $\Delta\phi$ is the phase difference between the two receivers. From eqn. (3) it follows $$Att_{T1} = -20\log\frac{G_2}{G_1} - 20\log\frac{A_2}{A_1}, \quad (4)$$

$$Pha_{T1} = \Delta\phi. \quad (5)$$

Thus, it is clear that the gain change affects attenuation measurement but not the phase difference measurement.

Similarly, attenuation measurement for the 2nd transmitter is derived from $$R_{T1} = \frac{G_1 H_2}{G_2 H_1} = \frac{G_1}{G_2} \frac{A_2}{A_1} e^{i\Delta\phi} \quad (6)$$

The attenuation measurement may be written as:

$$Att_{T1} = -20\log\frac{G_1}{G_2} - 20\log\frac{A_2}{A_1}. \quad (7)$$

Averaging equations (3) and (4) may remove the effect of gain variation. Those versed in the art would recognize that measurements of amplitude and phase can, in addition to resistivity determination, also be used for determining the dielectric constant of the earth formation.

Figure 3A:
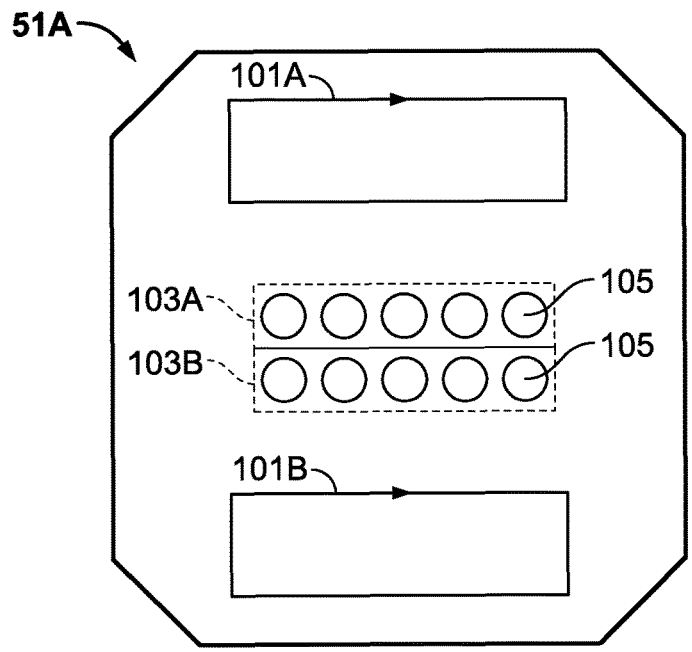
FIGS. 3A and 3B are schematics of antenna configurations for a pad of an electromagnetic tool for embodiments according to the present disclosure.

FIG. 3A shows a schematic of a generic tool configuration for one embodiment according to the present disclosure. Here, multiple receiver pairs of receivers may be used to achieve sufficient azimuthal coverage. Pad 51A may include two receiver arrays 103A, 103B. For each receiver 105 in the upper array 103A, there is a corresponding receiver 105 in the lower array 103B. In one embodiment, the coils 101A, 101B of the upper and lower receiver arrays may be aligned radially with respect to the tool axis (movement) direction. The receiver coils 105 are separated laterally by a constant distance that is determined by the azimuthal resolution of the electromagnetic tool. Two transmitting antennas 101A, 101B may be placed above receiver array 103A and below receiver array 103B. The transmitting antennas 101A, 101B may be operated one at a time during which measurements from each and every receiver pair are made. An exemplary current flow direction for the transmitters 101A, 101B is shown by the arrows in FIG. 3A. With the indicated current flow of the transmitters 101A, 101B and the coil orientation of the receivers 105, the measurements made would be xx-measurements. The measurements may include attenuation rate, phase difference, or compensated magnetic field.

Figure 3B:
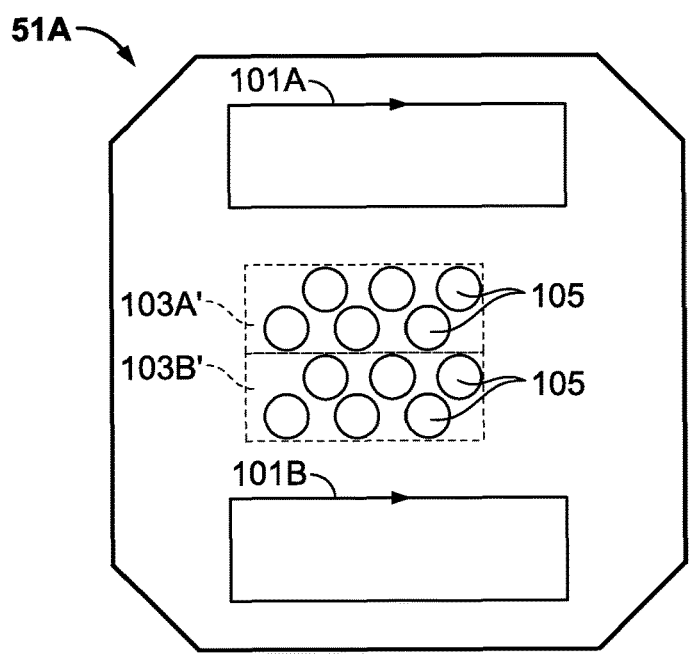

FIG. 3B shows a schematic of another embodiment of a generic tool configuration with staggered receiver pairs according to the present disclosure. Depending on the size of the receiver coils 105, the receiver pairs may be staggered in the tool axis direction, allowing a small separation between the receiver pairs. The upper receiver array 103A' may comprise two staggered rows of receivers 105 and the lower receiver array 103W may comprise two staggered rows of receivers 105 to reduce the gaps in azimuthal coverage of the configuration of FIG. 3A.

Figure 4A:
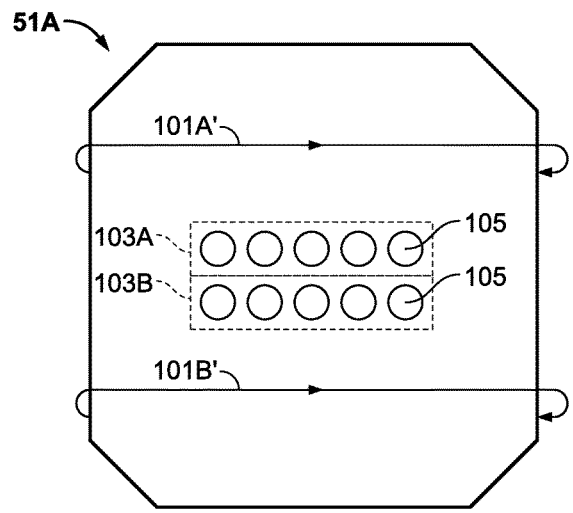
FIGS. 4A & 4B are schematics of an antenna configuration for a pad of an electromagnetic tool for other embodiments according to the present disclosure.

FIG. 4A is a schematic of a transmitter for one embodiment according to the present disclosure. Transmitters 101A' and 101W may have wires wound around the pad 51A. The wire paths may be substantially normal to the tool axis, going in the front, back, and on sides of the pad 51A. With the configuration shown in FIG. 4A, the measurements would be zx-measurements.

Figure 4B:
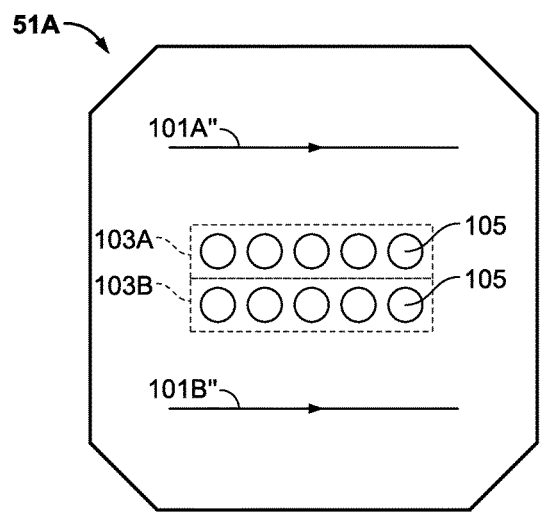

FIG. 4B is a schematic of a transmitter for another embodiment according to the present disclosure. Transmitters 101A", 101B" may be electric dipoles normal to the tool axis.

Figure 5:
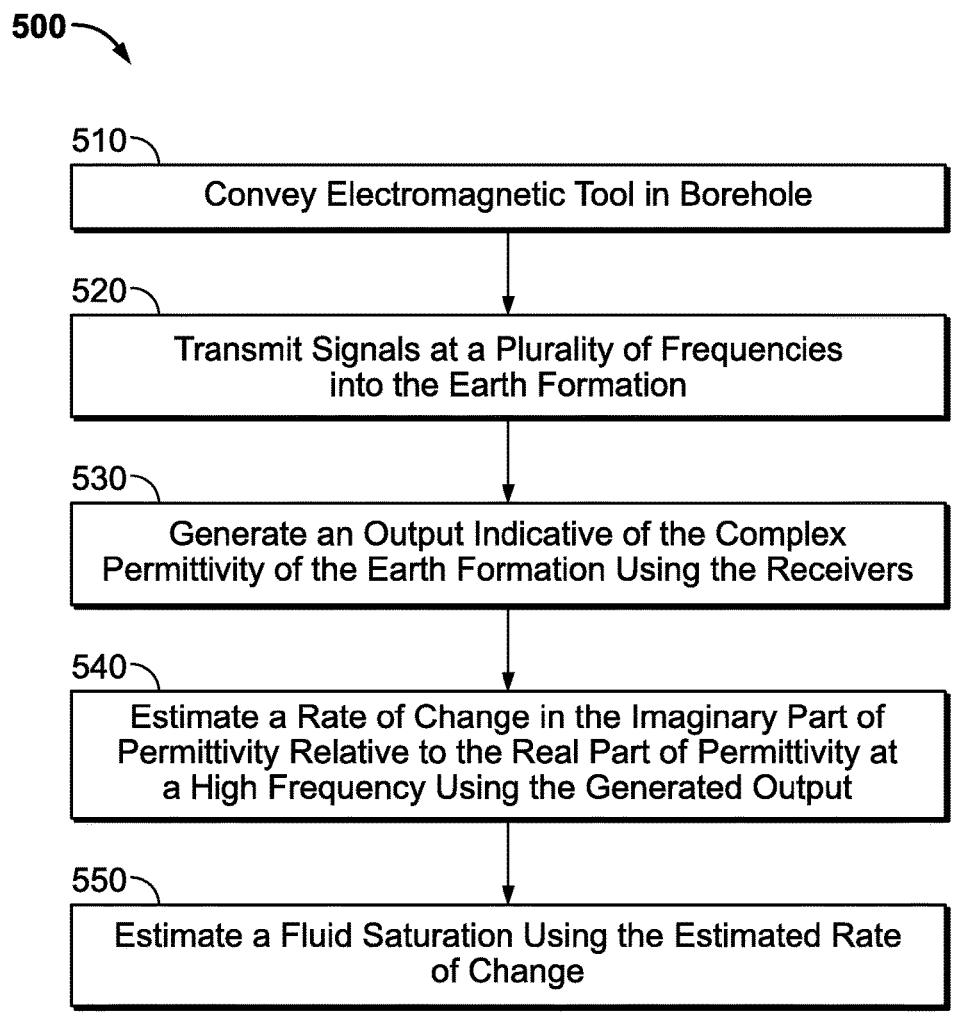
FIG. 5 is a flow chart for a method for one embodiment according to the present disclosure.

FIG. 5 is a flow chart of one method 500 for estimating a fluid saturation according to one embodiment of the present disclosure. In step 510, electromagnetic tool 51A may be conveyed in the borehole 12. In step 520, signals at a plurality of frequencies may be transmitted from transmitters 101A, 101B into the earth formation. In some embodiments, at least one of the plurality of frequencies may be at a frequency at or above 500 MHz. In step 530, receivers 103A, 103B may generate an output indicative the complex dielectric permittivity of the earth formation 13. In step 540, a rate of change of the imaginary part of the complex dielectric permittivity relative to the real part of the complex dielectric permittivity may be estimated using the generated output. In step 550, a parameter of interest may be estimated using the estimated rate of change.

The selection of the plurality of frequencies may include frequencies at or near the high frequency limit of the real part of dielectric permittivity for the particular polarization type of the earth formation. Several basic polarization types depending on colloid structure of oil, water contact with the containing porous medium, and water-oil contact in the containing medium can be identified. The physical bases in these cases correspond to migration polarization (the Maxwell-Wagner polarization) at the contacts between colloid particles in oil, polarization of the double layer and bulk charge at the contacts between water and the rock matrix of the containing porous medium, etc. Each polarization type may be identified with a specific structural unit of the medium and cataloged in the dielectric spectra. Determination of the particle type in the colloid solution in the porous medium may be then reduced to the problem of identification of the cataloged and the measured spectra. It should be noted that polarization types may be reduced to the following three basic polarization types.

Havriliak-Negami relaxation (its specific cases are the Cole-Davidson, Debye, and Cole-Cole relaxations) characterized by frequency dependence of the complex value of dielectric permittivity may be expressed as:

$$\varepsilon^* = \varepsilon_\infty + (\varepsilon_s - \varepsilon_\infty)[1+(i\omega\tau)^{1-\alpha}]^{-\beta} \quad (8)$$

$$\varepsilon^* = \varepsilon' - i\varepsilon'' \quad (9)$$

m-th power law relaxation $$\varepsilon^* = A \cdot (i\omega)^{-m} \quad (10)$$

and Maxwell-Wagner relaxation $$\varepsilon^* = \varepsilon_\infty + 4\pi\sigma/i\omega + (\varepsilon_s - \varepsilon_\infty)/(1+i\omega\tau) \quad (11).$$

Figure 6:
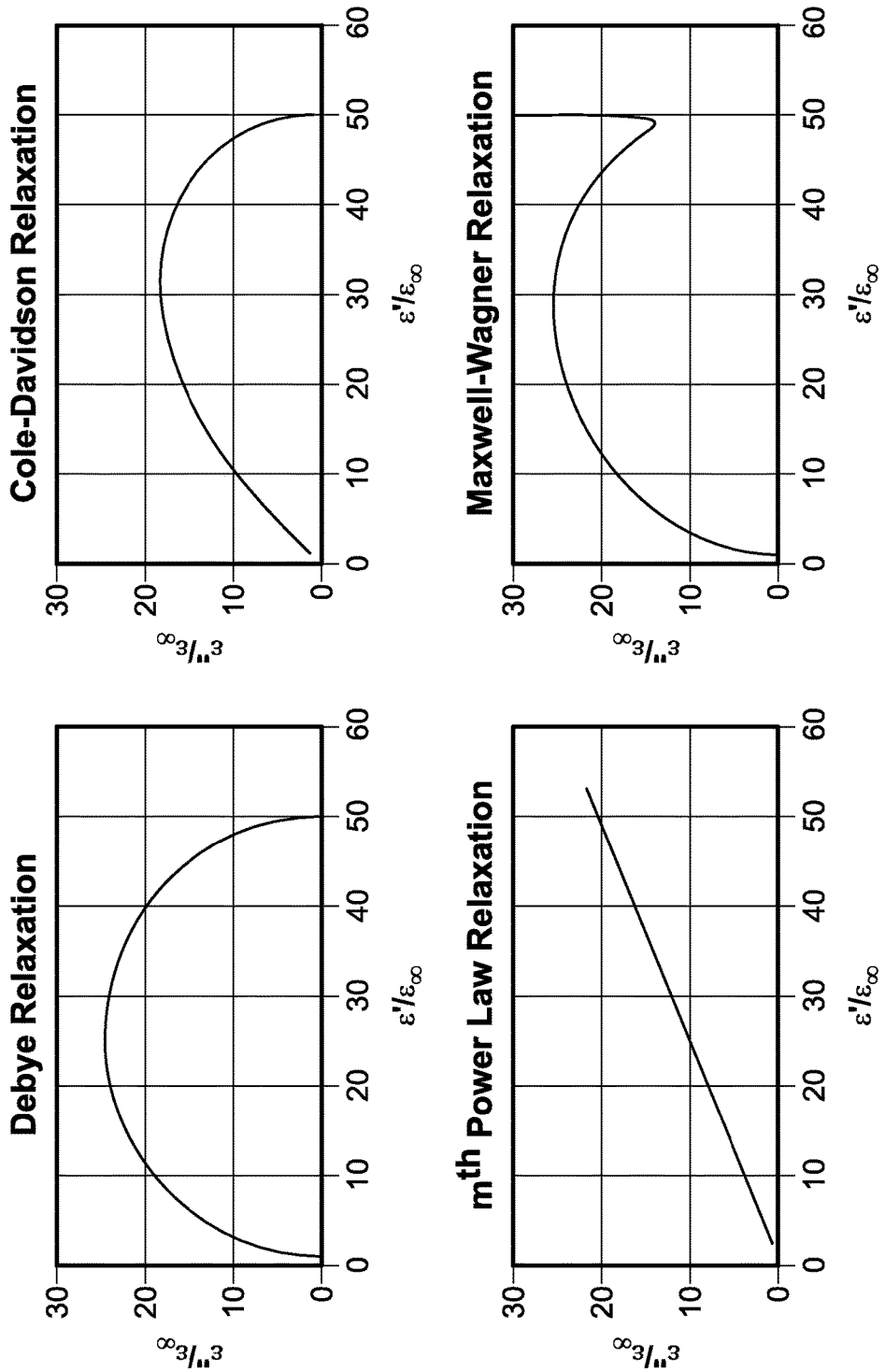
FIG. 6 is a set of graphs showing relaxations for different polarization types for one embodiment according to the present disclosure.

FIG. 6 shows a set of complex permittivity curves depicting spectral images of dielectric permittivity for different relaxations related to polarization types and associated with colloidal structure of fluid within a saturated porous medium. The Maxwell-Wagner relaxation determines the phase of colloid particles, the m-th power law relaxation corresponds to laminated or disk-shaped micellar colloid particles, the Debye relaxation corresponds to crystalline solid colloid particles, the Cole-Davidson relaxation corresponds to local crystalline structuring in colloid particles, etc. Having compiled the catalog of polarization types, the structure of water-hydrocarbon mixture and colloid oil contents in the saturated porous medium may be identified. The structure of the water-oil mixture may be indicative of permeability of the earth formation. For example, water-saturated sandstones and dolomites may have a polarization type that demonstrates Cole-Cole relaxation. The polarization type may be identified using electromagnetic logging of the borehole. In the kHz range, fresh water-saturated porous media may be characterized by high dielectric permittivity (up to $10^3$-$10^4$) at characteristic relaxation frequencies.

Figure 7:
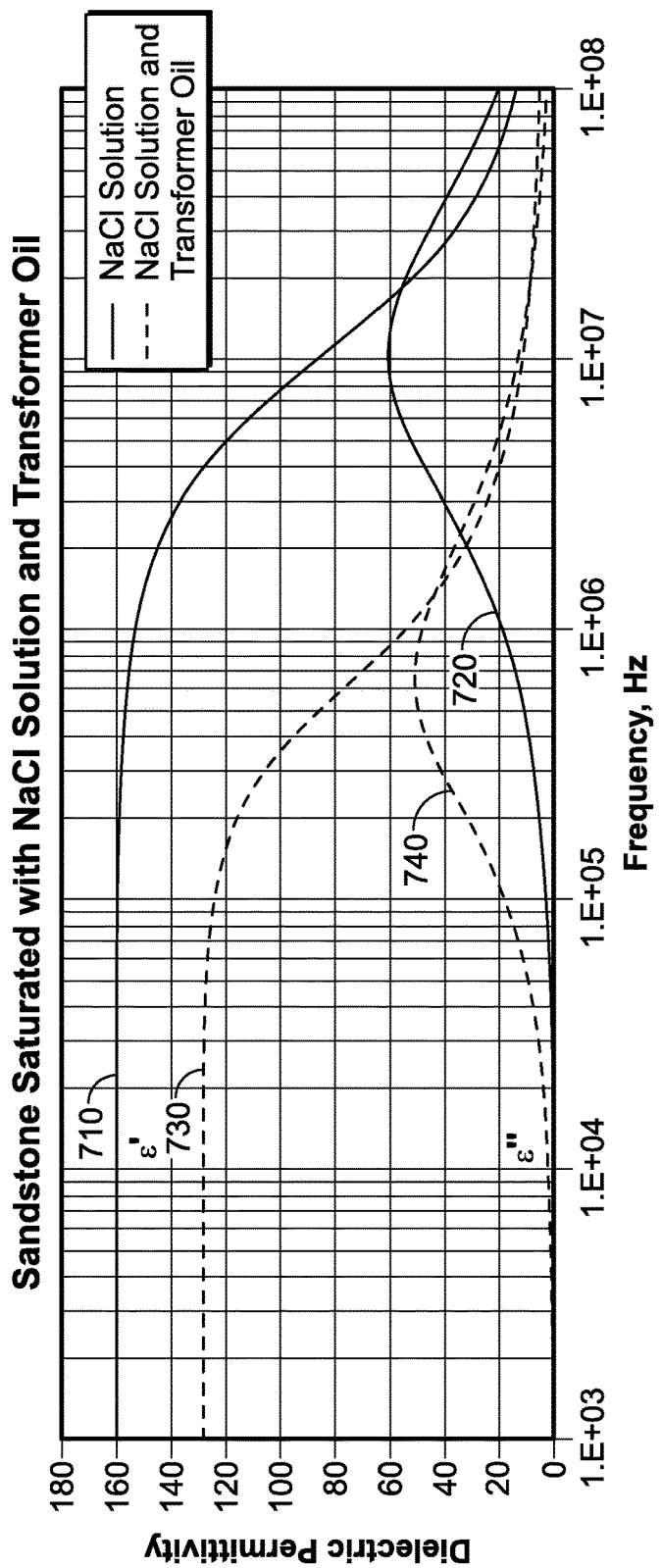
FIG. 7 is a graph of complex permittivity for water and water/oil saturated sandstone for one embodiment according to the present disclosure.

FIG. 7 shows a chart with a set of curves representing the frequency dependence complex dielectric permittivity of sandstone saturated with (i) water and (ii) a mixture of water and transformer oil. Curve 710 indicates the real part of dielectric permittivity for sandstone saturated with water. Curve 720 indicates the imaginary part of dielectric permittivity for sandstone saturated with water. Curve 730 indicates the real part of dielectric permittivity for sandstone saturated with a mixture of water and transformer oil. Curve 740 indicates the imaginary part of dielectric permittivity for sandstone saturated with a mixture of water and transformer oil.

In the case when both water and mixed phase hydrocarbons are present in the earth formation 13, step 750 may include finding a bulk fraction of water if there are no mixed phase hydrocarbons and a bulk fraction of water in the presence of mixed phase hydrocarbons. The difference between these two values may yield the bulk fraction of mixed phase hydrocarbons. The method of finding water saturation and hydrocarbon saturation is illustrated below using the cases of the Cole-Cole relaxation and the Havriliak-Negami relaxation. The estimate of the dielectric permittivity may assume a natural porous medium, such as sandstone or dolomite, that is saturated with water and assuming that the dielectric polarization type of this system was established via borehole measurements.

As described above, for an earth formation comprising a porous medium saturated with a mixture of water and a plurality of hydrocarbon phases (e.g., a mixture of water, oil, and gas) each of the imaginary part and the real part of an estimate of complex permittivity may vary in dependence upon the frequency of the electrical signal used in making the estimate. After making several estimates over a range of frequencies, it is possible to estimate parameters of interest of the earth formation by characterizing the relationship of changes in both the real and imaginary parts of the estimates with frequency. For example, parameters of interest may be estimated using techniques related to a rate of change of between estimates of a plurality of estimates of complex permittivity of an imaginary part relative to a real part of each estimate. Method embodiments may include generating a spectral dielectric curve by mapping the real part with respect to the imaginary part for each estimate of the plurality of estimates.

Figure 8:
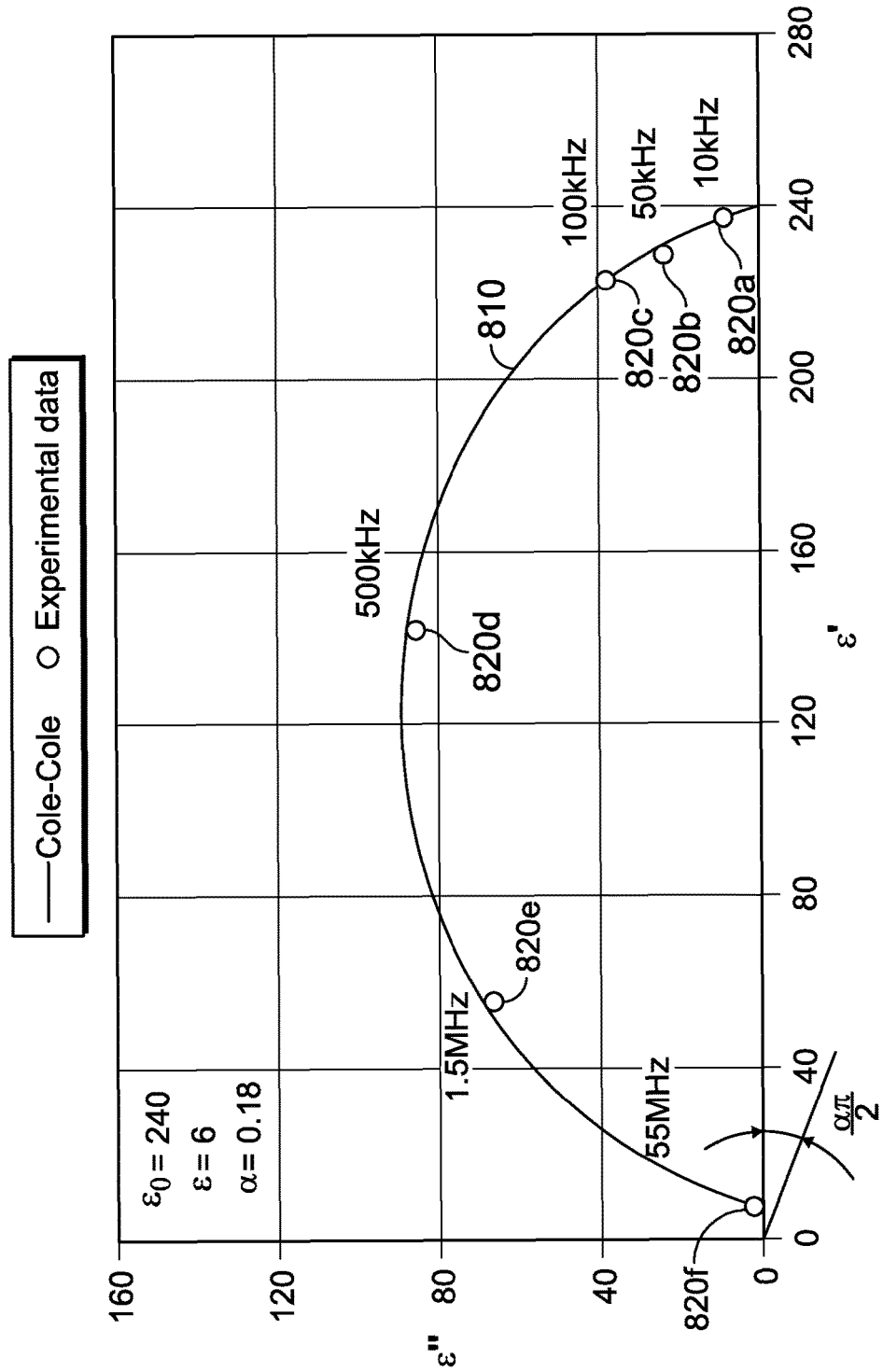
FIG. 8 is a graph of imaginary versus real parts of complex permittivity for water and water/oil saturated sandstone for one embodiment according to the present disclosure.

FIG. 8 shows an exemplary set of curves for sandstone expressing complex dielectric permittivity over a range of frequencies. In water-saturated sandstones, the Cole-Cole relaxation is typically observed as shown in as curve 810. The dielectric spectra may be characterized by a symmetrical polarization curve of the Cole-Cole type (the curve on the plane $\varepsilon''$, $\varepsilon'$) as expressed by the formula:

$$\varepsilon = \varepsilon_\infty + \frac{\varepsilon_s - \varepsilon_\infty}{1 + (i\omega\tau)^{1-a}} \quad (12)$$

where $\varepsilon$ is complex dielectric permittivity, $\varepsilon_0$, the asymptotic value of the real part of this polarization type at high frequencies, $\varepsilon_s$ is the static value of dielectric permittivity, $\tau$ is relaxation time, a is a parameter ranging from 0 to 1, which characterizes the polarization angle. It has been established experimentally that natural media like sandstones or dolomites demonstrate that the asymptotic value of the real part of dielectric permittivity depends only on water saturation of the pore space and does not depend on the saline concentration in saturating water and rock type. In other words, $\varepsilon_\infty$ is a universal function of water saturation of the porous rock. Frequency dependencies of the real and imaginary parts of dielectric permittivity for water-saturated formations (real part, imaginary part) shown in curve 810 appear to be symmetrical with respect to the maximum of the imaginary part of dielectric permittivity. Curve 820 may represent the Havriliak-Negami relaxation observed when oil is present.

Novel aspects of the present disclosure further include the determination that curve 820 may also represent the Havriliak-Negami relaxation observed when mixed phase hydrocarbons are present, due to the similarities in the dielectric constant between mixed phase hydrocarbons (particularly oil and gas) and oil alone. Thus, when hydrocarbons are present, the symmetry in the high frequency domain may no longer remain, as is shown with curve 820, and distortion angles 830, 840 between each of the spectral dielectric curves 810, 820 and the x-axis may depend on the bulk fraction of hydrocarbons present in the formation. Distortion may be obtained from the spectral dependences of the dielectric constant (the real and imaginary parts) in the low frequency domain. Knowing the distortion angle, the bulk fraction of hydrocarbons present in the formation may be determined. Experimental data points 820a-f (at 10 kHz, 50 kHz, 100 kHz, 500 kHz, 1.5 MHz, and 55 MHz, respectively) confirm the close relationship between practice and the Cole-Cole relaxation in curve 810.

Thus, with the spectral dielectric image determined it is possible to obtain all spectral characteristics of dielectric permittivity consistent with the Havriliak-Negami dependence, including the key polarization parameters $\alpha$ and $\beta$. Taking the polarization parameter $\beta$ of Havriliak-Negami polarization to represent a mixed hydrocarbon fraction, using techniques of the present disclosure it is possible to calculate the second polarization parameter $\alpha$, from which water saturation and bulk fraction of water may be determined.

For Cole-Cole relaxation it is known that:

$$\varepsilon_{max}'' = (\varepsilon_s - \varepsilon_\infty) \cdot \tan[(1-\alpha)\pi/4]/2 \tag{13}$$

where $\varepsilon_{max}''$ is the maximal loss factor, s is the static value of the real part of dielectric, $\varepsilon_\infty$ is its high-frequency limit, and a is the polarization parameter. It is also known, for Cole-Cole relaxation, that the following relationship is true.

$$\varepsilon_s = 2\varepsilon_{max}' - \varepsilon_\infty \tag{14}$$

Using eqns. (13) and (14), it follows that:

$$\varepsilon_\infty = \varepsilon_{max}' - \varepsilon_{max}''/\tan[(1-\alpha)\pi/4]/2 = \varepsilon_\infty(K) \tag{15}$$

where $\varepsilon_\infty(K)$ is a given universal function of water saturation (water fraction in percent). The universal curve $\varepsilon_\infty(K\%)$ may be obtained via laboratory experiments, and $\varepsilon_{max}''$, $\varepsilon_{max}'$, $\alpha$ may be obtained via inductive logging.

If water and mixed phase hydrocarbons are present in the porous space, for example as a water-oil mixture and gas as a separate phase, the polarization curve may be estimated as the Havriliak-Negami formula as shown as curve 820 in FIG. 8 and expressed as follows.

$$\varepsilon^* = \varepsilon_\infty + \frac{\varepsilon_s - \varepsilon_\infty}{[1 + (i\omega\tau)^{1-\alpha}]^\beta} \tag{16}$$

where there are two polarization parameters: $\alpha$ and $\beta$.

The presence of the $\beta$ term may result in the high-frequency limit of the real part of complex dielectric permittivity depending in part on mixed phase hydrocarbon content. For small distortions of the left angle in curve 820, expansion with respect to the power indices $\beta-1$ may be performed with the accuracy of quadratic terms and has the following form:

$$\varepsilon_\infty = \varepsilon_{\infty,0} + \varepsilon_s(\beta-1)/2 + \tag{17}$$

The first term of this expansion may describe angle distortions correctly up to the values of $\beta=0.7$. In the case of a further decrease of $\beta$, the quadratic terms are to be taken into account. When hydrocarbons are present in the porous space, water saturation may be calculated for the no-oil case $K_{water}$ using the right hand angle. Polarization parameters $\varepsilon_{max}''$ and $\varepsilon_{max}'$ may be found via the right hand angle. Based on the polarization curve for the oil case, $\beta=0.7$ may be calculated using the eqn (13).

This example using the Cole-Cole relaxation case is illustrative and exemplary only, as other polarization types may be used, including, but not limited to, Debye relaxation, Cole-Davidson relaxation, m-th power law relaxation, and Maxwell-Wagner relaxation.

Comparative analysis of the spectral dependence of the water-oil-and-gas-saturated porous media and the spectra of water-oil emulsions shows that, in the porous medium, oil seems to have the form of water-oil emulsion, i.e. there are droplets of oil in water inside the pores. The physics of polarization losses in the MHz range is as follows.

The Debye polarization (a special case of the Cole-Cole polarization with a single relaxation time of the corresponding distribution function) characterizes polarization in the system of independent oscillators in the external electric field. Asymmetry of the Debye polarization curve is related to the Cole-Davidson polarization curve. The physics behind this deformation of the polarization curve may be emerging non-linear interaction in the system of independent oscillators (polarizing dipoles in the external electric field). The analysis of the experimental spectral data for dielectric permittivity of the porous media saturated with water-oil mixture and for water-oil emulsions appears to indicate that, in the porous media, oil takes the form of droplets in water, i.e. a system similar to that of water-oil emulsions in the porous media.

More generally, the dielectric polarization spectrum for a porous reservoir formed by rock (sandstones, carbonates, etc.) saturated with oil and water mixture with gas as a separate phase may have the form of Havriliak-Negami spectral dependence:

$$\varepsilon^* = \varepsilon_\infty + \frac{\varepsilon_0 - \varepsilon_\infty}{[1 + (i\omega\tau)^{1-a}]^b}. \tag{18}$$

In this formula, $\varepsilon^* = \varepsilon' + i\varepsilon''$ is the complex value of dielectric permittivity; $\varepsilon_\infty$ is an asymptotic value ($\omega=\infty$) of dielectric permittivity; $\varepsilon_0$ is an asymptotic value ($\omega=0$) of dielectric permittivity; $\tau$ is relaxation time; $\omega$ is the frequency of electromagnetic excitation of the medium; and a and b are parameters characterizing the porous medium ($0 \leq a < 1$; $1 \geq b > 0$).

The Cole-Cole diagram shows that the $\varepsilon''(\varepsilon')$ dependence has the form of an arc with an asymmetrically sloped left side (FIG. 8). Assuming that the curve shows the spectral characteristics of the Havriliak-Negami relaxation curve, experimental results show that $$v = \frac{2\varepsilon_{max}''}{\varepsilon_0 - \varepsilon_\infty} \tag{19}$$

for the porous reservoir saturated with water at different levels of saturation with oil and also gas as a separate phase. Thus, v may be estimated as a function of the spectral dielectric curve and asymptotic values ($\varepsilon=\varepsilon_0$, $\varepsilon=\varepsilon_\infty$) for the real parts of each estimate of the spectral dielectric curve and a maximum imaginary value for the spectral dielectric curve ($\varepsilon_{max}''$). We assume that, in the presence of gas, the character of the curve does not change in the frequency range selected below for finding polarization parameters.

Based on the measured characteristics $\varepsilon_\infty$, $\varepsilon_0$, $\tau$, $\alpha$, $\beta$, we plot the dielectric spectrum $\varepsilon''(\varepsilon')$ and calculate v. Note that this value does not seem to change with changes in proportions of hydrocarbon versus water saturation for the same porous medium. Thus, v is a spectral dielectric curve constant that characterizes a reservoir saturated with water.

The following dependence holds true for the Havriliak-Negami relaxation:

$$v = \frac{2\varepsilon_{max}''}{\varepsilon_0 - \varepsilon_\infty} = tg\left(\frac{1-\alpha}{4}\pi\right) \cdot \chi(B), \tag{20}$$

-continued $$\chi(B) = 2\left[\text{Sin}\frac{\beta r}{2(1+\beta)}\right]^{1+\beta}.$$

The parameter β may be considered as the parameter characterizing the degree to which the porous formation is saturated with hydrocarbons (e.g., gas and oil), in the presence of water. Its value determines the value of the parameter $\alpha=\alpha(\beta)$. Thus, solving equations (20) for $\alpha=\alpha(\beta)$, we can find dependence $$\alpha(\beta) = 1 - \frac{4}{\pi}\text{arc}tg\frac{v}{\chi(\beta)}. \quad (21)$$

Figure 9A:
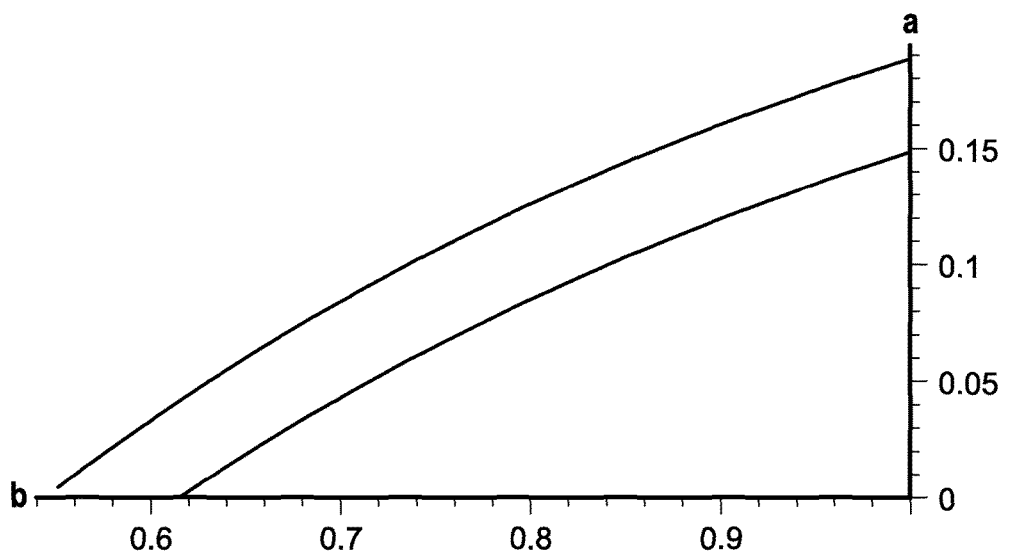
FIG. 9A shows the graph of $\alpha = \alpha(\beta)$ for two values of v.
Figure 9B:
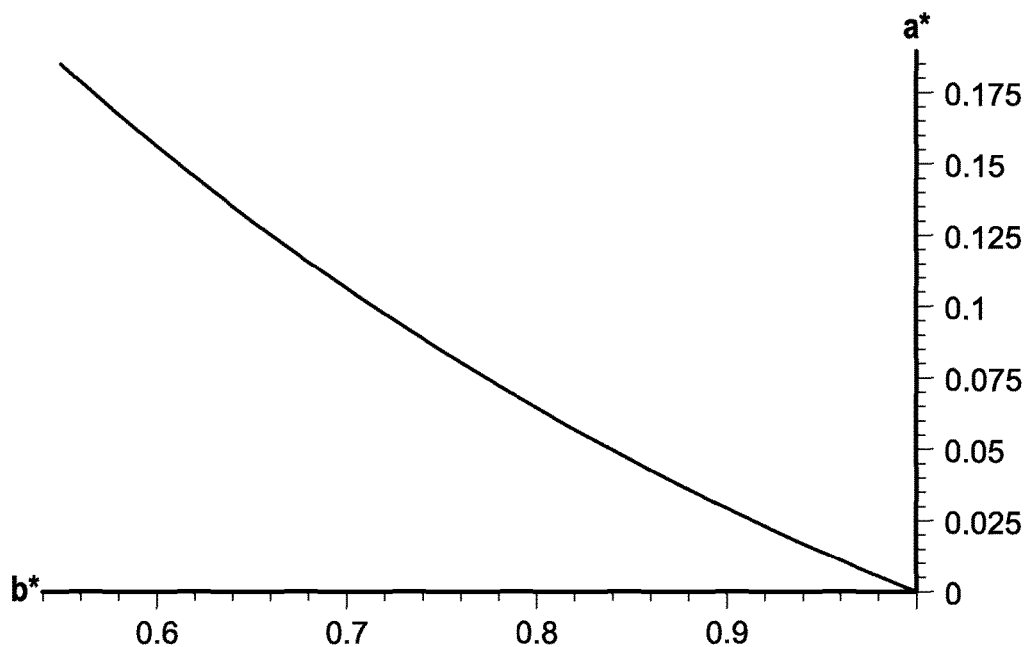
FIG. 9B shows the graph of $\alpha_* = \alpha_*(\beta_*)$.
Figure 9C:
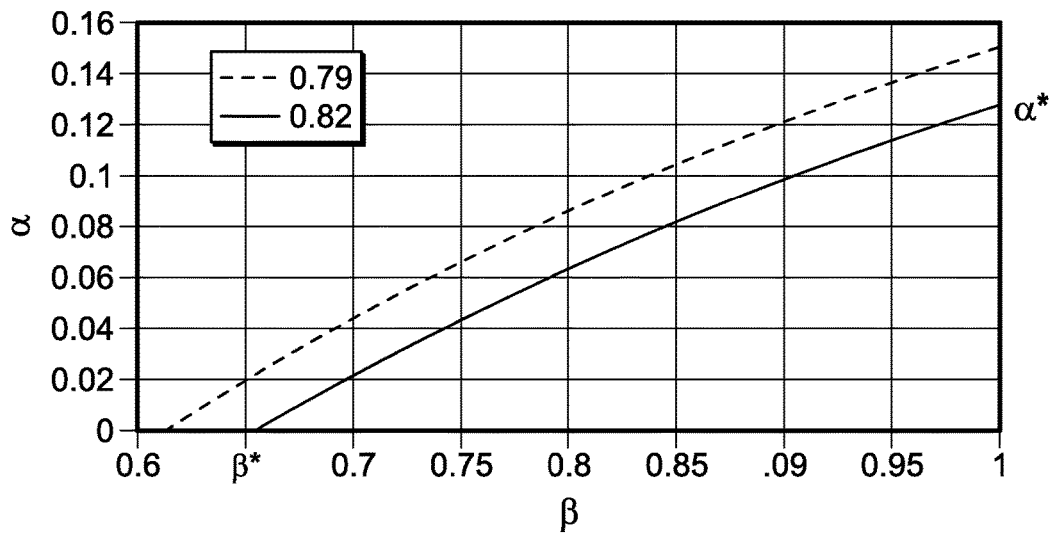
FIG. 9C shows the graph of $\alpha = \alpha(\beta)$ for two values of v where $\beta$ relates to a degree of saturation of the porous medium with a plurality of hydrocarbon phases in the presence of water.

The parameter v depends on rock porosity and lithology, as well as on the electrochemical characteristics of the contact between water and rock, for the porous medium. FIG. 9A shows the graph of $\alpha=\alpha(\beta)$ for two values of v. FIG. 9B shows the graph of $\alpha_*=\alpha_*(\beta_*)$. The hydrocarbon saturation variable β varies from 1 to $\beta_*$. The point $\beta=1$ corresponds to the state of the medium with no hydrocarbons in the reservoir. The point $\beta=\beta_*$ corresponds to the state of the reservoir saturated with hydrocarbons only (no water). The current value of β, $\beta_0$, corresponds to the current value of α, $\alpha_0$, found for any v, as calculated above. The parameter α may vary from 0 to $\alpha_*$, as is apparent from the graph. The point $\alpha=0$ corresponds to the state of the medium with no water in the water-hydrocarbon mixture. The point $\alpha=\alpha_*$ corresponds to the state of the reservoir with no hydrocarbons (water only), in which case water fraction is correlated with porosity. FIG. 9C shows the dependence of $\alpha=\alpha(\beta)$ for two values of v, 0.79 and 0.82.

The parameters $\alpha_*$ and β are related as follows:

$$\alpha_* = 1 - \frac{4}{\pi}\text{arc}tg[\chi(\beta_*)]. \quad (22)$$

Hydrocarbon saturation corresponds to 1−β with a possibility of hydrocarbon saturation reaching $1-\beta_*$. Water saturation corresponds to a with a possibility of water saturation reaching $\alpha_*$. Therefore, the formation porosity $K_f$ may be described with the following formula:

$$K_f = \alpha_* \cdot 100\% \quad (23)$$

the bulk water fraction may be described with the following formula:

$$K_{water}(\%) = \frac{\alpha}{\alpha_*} \cdot 100\% \quad (24)$$

and the bulk hydrocarbon fraction may be described with the following formula:

$$K_h = \left(1 - \frac{\alpha}{\alpha_*}\right) \cdot 100\%. \quad (25)$$

Formation porosity is water saturation at $\beta=1$, and may be estimated based on $\alpha=\alpha_*$. Under the lab conditions, for example, for a variety of lithologies (water-saturated sandstones, carbonates, dolomites, etc.), dependence of $\alpha_*$ on water saturation or on pore volume $K_p$, may be measured ($K_p=\alpha_* \cdot 100\%$). A table may be created relating the dependence $\alpha_*=\alpha_*(K_p)$. Advantageously, it is possible to estimate $\alpha_0$, and v for $\beta_0$ under borehole conditions, given the known relationship of the polarization characteristics $\varepsilon_\infty$, $\varepsilon_0$, τ, α, β. Similarly, from Eqn. (22) it is possible to calculate $\alpha_*$ using $\beta_*$ ($\beta_*=1$).

Examples of estimated values may include, for sandstones:

$2\varepsilon_{max}''/\Delta\varepsilon=0.79$, $\alpha_*=0.14$, $K_p=\alpha_* \cdot 100\%=14$ percent which approximates an experimentally derived value of 14.1 percent, and for dolomites:

$2\varepsilon_{max}''/\Delta\varepsilon=0.74$, $\alpha_*=0.18$, $K_p=\alpha_* \cdot 100\%=18$ percent which approximates an experimentally derived value of 16.9 percent.

Any current value of β may help compare water fraction (percent) in a water—and mixed phase hydrocarbon-saturated porous reservoir using equations (25), and porosity may be determined from the tabulated curve.

Figure 10:
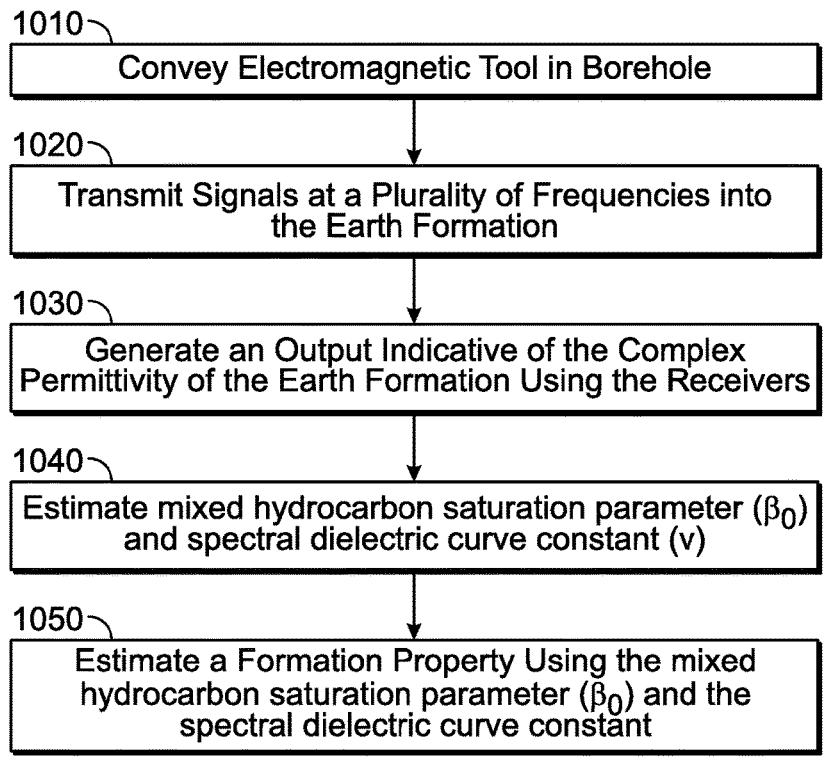
FIG. 10 is a flow chart for a method for one embodiment according to the present disclosure.

FIG. 10 is a flow chart of one method 1000 for estimating changes in water fraction in the water-hydrocarbon reservoir and its porosity according to one embodiment of the present disclosure. In step 1010, electromagnetic tool 51A may be conveyed in the borehole 12. In step 1020, signals at a plurality of frequencies may be transmitted from transmitters 101A, 101B into the earth formation. In some embodiments, at least one of the plurality of frequencies may be at a frequency at or above 500 MHz. In step 1030, receivers 103A, 103B may generate an output indicative the complex dielectric permittivity of the earth formation 13. In step 1040, mixed hydrocarbon saturation parameter ($\beta_0$) and spectral dielectric curve constant (v) may be estimated using the generated output. In step 1050, at least one of the formation porosity, the bulk hydrocarbon fraction, and the water fraction may be estimated (as shown in Eqns. 23-25) using the estimated parameters $\alpha_0$, calculated from $\beta_0$ and v using Eqn. 21, and $\alpha_*$, which corresponds to a value of the mixed hydrocarbon saturation parameter for a complete water saturation point ($\beta=1$) and is similarly calculated.

One of skill in the art, with the benefit of the teachings in this disclosure, would understand that different polarization curves may be used depending on lithology, such as, but not limited to, the Cole-Davidson polarization curve.

As described herein, the method in accordance with the presently disclosed embodiment of the disclosure involves several computational steps. As would be apparent by persons of ordinary skill, these steps may be performed by computational means such as a computer, or may be performed manually by an analyst, or by some combination thereof. As an example, where the disclosed embodiment calls for selection of measured values having certain characteristics, it would be apparent to those of ordinary skill in the art that such comparison could be performed based upon a subjective assessment by an analyst or by computational assessment by a computer system properly programmed to perform such a function. To the extent that the present disclosure is implemented utilizing computer equipment to perform one or more functions, it is believed that programming computer equipment to perform these steps would be a matter of routine engineering to persons of ordinary skill in the art having the benefit of the present disclosure.

Implicit in the processing of the acquired data is the use of a computer program implemented on a suitable computational platform (dedicated or general purpose) and embodied in a suitable machine readable medium that enables the processor to perform the control and processing. The term "processor" as used in the present disclosure is intended to encompass such devices as microcontrollers, microprocessors, field-programmable gate arrays (FPGAs) and the storage medium may include ROM, RAM, EPROM, EAROM, solid-state disk, optical media, magnetic media and other media and/or storage mechanisms as may be deemed appropriate. As discussed above, processing and control functions may be performed downhole, at the surface, or in both locations.

From the foregoing disclosure, it should be apparent that a method and apparatus for evaluating an earth formation has been disclosed involving the measurement of electrical characteristics including formation dielectric permittivity and involving measurements taken at a plurality of measurement frequencies.

Although a specific embodiment of the disclosure as well as possible variants and alternatives thereof have been described and/or suggested herein, it is to be understood that the present disclosure is intended to teach, suggest, and illustrate various features and aspects of the disclosure, but is not intended to be limiting with respect to the scope of the disclosure, as defined exclusively in and by the claims, which follow.

While the foregoing disclosure is directed to the specific embodiments of the disclosure, various modifications will be apparent to those skilled in the art. It is intended that all such variations within the scope of the appended claims be embraced by the foregoing disclosure.

What is claimed is:

1. A method of finding at least one of a porosity of an earth formation including a porous medium, a combined hydrocarbon bulk fraction in the medium, or a bulk fraction of water in the medium, by means of dielectric spectroscopy, the method comprising:
conveying a carrier in a borehole penetrating the earth formation;
performing dielectric spectroscopy by making a plurality of estimates of complex permittivity based on measurements using an electromagnetic tool disposed on the carrier at a plurality of frequencies in a borehole penetrating the earth formation while the porous medium of the formation is saturated with a mixture of water and combined hydrocarbons comprising a plurality of hydrocarbon phases including oil and gas; and
estimating a property of the earth formation with at least one processor using the plurality of estimates by modeling the porous medium of the formation as saturated with a mixture of water and the combined hydrocarbons and by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate;
wherein the property comprises at least one of: (i) the combined hydrocarbon bulk fraction; (ii) the bulk fraction of water; and (iii) the porosity.

2. The apparatus of claim 1 wherein three of the at least three collocated antennas are orthogonal with respect to one another.

3. The method of claim 2, wherein the spectral dielectric curve constant (v) is calculated using a maximum imaginary value for the spectral dielectric curve and asymptotic values ($\in=\in_0$, $\in=\in_\infty$) for the real parts of each estimate of the spectral dielectric curve.

4. The method of claim 2, comprising using a model correlating the plurality of estimates to a Havriliak-Negami relaxation curve to determine a value for at least one polarization parameter associated with the curve.

5. The method of claim 4, wherein the at least one polarization parameter comprises $\beta$, wherein $\beta$ relates to a degree of saturation of the porous medium with the plurality of hydrocarbon phases in the presence of water.

6. The method of claim 5, comprising determining the value for $\beta$ using an angle of intersection ($\varphi$) of two curves Im $\in=\Phi(\text{Re }\in)$ and Im $\in=0$ at the point where $\in=\in_0$ and a second angle of intersection ($\varphi$) of the two curves Im $\in=\Phi(\text{Re }\in)$ and Im $\in=0$ at the point where $\in=\in_\infty$.

7. The method of claim 5, comprising using the spectral dielectric curve constant (v) and the value for $\beta$ to determine a value for another polarization parameter $\alpha$, wherein $\alpha$ relates to a degree of saturation of the porous medium with water, and wherein $\alpha$ relates to a polarization angle.

8. The method of claim 7, comprising determining values $\alpha 0$ and $\alpha^*$ for a using a relationship defining a as a function of $\beta$, wherein $\alpha 0$ corresponds to the value for $\beta$ ($\beta 0$) and $\alpha^*$ corresponds to a second value for beta correlated with a state of the porous medium free from the plurality of hydrocarbon phases.

9. The method of claim 8, comprising using the values $\alpha 0$ and $\alpha^*$ to estimate a bulk water fraction of the porous medium.

10. The method of claim 8, comprising using the values $\alpha 0$ and $\alpha^*$ to estimate a bulk hydrocarbon fraction of the porous medium.

11. The method of claim 7, comprising:
determining a value $\alpha^*$ for a using a relationship defining a as a function of $\beta$, wherein $\alpha^*$ corresponds to a second value for beta correlated with a with a state of the porous medium free from the plurality of hydrocarbon phases; and
using the value $\alpha^*$ to estimate a porosity of the porous medium.

12. The method of claim 2, further comprising using the electromagnetic tool for making the measurements at the plurality of frequencies.

13. The method of claim 2, further comprising:
inverting the measurements to generate the imaginary part and the real part of each estimate of complex permittivity at the plurality of frequencies; and
estimating the rate of change of the imaginary part relative to the real part from one of the estimates to another of the estimates.

14. The method of claim 1, wherein the electromagnetic tool uses electrical induction.

15. The method of claim 1, further comprising performing further operations in dependence upon the parameter of interest, the further operations comprising at least one of:
i) recording the parameter of interest;
ii) displaying the parameter of interest;
iii) modifying a drilling operation in the earth formation;
iv) modifying a recovery operation in the earth formation.

16. An apparatus for finding at least one of a porosity of an earth formation including a porous medium, a combined hydrocarbon bulk fraction in the medium, or a bulk fraction of water in the medium, by means of dielectric spectroscopy, the apparatus comprising:
a carrier configured to be conveyed in a borehole penetrating the earth formation;
an electromagnetic tool disposed on the carrier and configured to make measurements indicative of an imaginary part and a real part of a permittivity of the earth formation at a plurality of frequencies; and at least one processor configured to:

perform dielectric spectroscopy by making a plurality of estimates of complex permittivity based on the measurements using the electromagnetic tool at the plurality of frequencies in the borehole while the porous medium of the formation is saturated with a mixture of water and combined hydrocarbons comprising a plurality of hydrocarbon phases including oil and gas; and estimate a property of the earth formation with at least one processor using the plurality of estimates by modeling the porous medium of the formation as saturated with a mixture of water and the combined hydrocarbons and by using a spectral dielectric curve constant (v) for the porous medium, the spectral dielectric curve constant (v) invariant with respect to a ratio of water to hydrocarbons in the porous medium and determined by an estimated rate of change between estimates of the plurality of estimates of complex permittivity of an imaginary part relative to a real part of each estimate;

wherein the property comprises at least one of: (i) the combined hydrocarbon bulk fraction; (ii) the bulk fraction of water; and (iii) the porosity.

* * * * *